US009044754B2

(12) United States Patent
Kumar et al.

(10) Patent No.: US 9,044,754 B2
(45) Date of Patent: Jun. 2, 2015

(54) MICRO CHIP

(75) Inventors: Kishore Krishna Kumar, Bangalore (IN); Raviprakash Jayaraman, Bangalore (IN); Sankaranand Kaipa Narasimha, Bangalore (IN); Renjith Mahiladevi Radhakrishnan, Bangalore (IN); Sathyadeep Viswanathan, Bangalore (IN); Chandrasekhar Bhaskaran Nair, Bangalore (IN); Pillarisetti Venkata Subbarao, Bangalore (IN); Manjula Jagannath, Bangalore (IN); Shilpa Chennakrishnaiah, Bangalore (IN)

(73) Assignee: Bigtec Private Limited, Bangalore, Karnataka (IN)

( * ) Notice: Subject to any disclaimer, the term of this patent is extended or adjusted under 35 U.S.C. 154(b) by 588 days.

(21) Appl. No.: 12/682,581

(22) PCT Filed: Oct. 13, 2008

(86) PCT No.: PCT/IN2008/000666
§ 371 (c)(1),
(2), (4) Date: Apr. 9, 2010

(87) PCT Pub. No.: WO2009/047805
PCT Pub. Date: Apr. 16, 2009

(65) Prior Publication Data

US 2010/0240044 A1 Sep. 23, 2010

(30) Foreign Application Priority Data

Oct. 12, 2007 (IN) ........................ 02311/CHE/2007
Oct. 12, 2007 (IN) ........................ 02312/CHE/2007
Oct. 12, 2007 (IN) ........................ 02313/CHE/2007
Oct. 12, 2007 (IN) ........................ 02314/CHE/2007
Oct. 15, 2007 (IN) ........................ 02328/CHE/2007

(51) Int. Cl.
*C12Q 1/68* (2006.01)
*B01L 7/00* (2006.01)
*C04B 35/00* (2006.01)
*B01L 3/00* (2006.01)

(52) U.S. Cl.
CPC ................ *B01L 7/52* (2013.01); *B01L 3/5027* (2013.01); *B01L 2300/0627* (2013.01); *B01L 2300/0851* (2013.01); *B01L 2300/0887* (2013.01); *B01L 2300/16* (2013.01); *B01L 2300/1805* (2013.01)

(58) Field of Classification Search
USPC ........................................................ 435/91.2
IPC ............ C12Q 1/686; B01L 7/525; C04B 35/00
See application file for complete search history.

(56) References Cited

U.S. PATENT DOCUMENTS 5,382,931 A * 1/1995 Piloto et al. .................. 333/208
5,455,385 A * 10/1995 Newton et al. ................ 174/559
5,708,570 A * 1/1998 Polinski, Sr. ................. 361/762

OTHER PUBLICATIONS

Kricka (Anal Bioanal Chem, 2003, vol. 377, p. 820-825).*
Golonka (Sensors and Actuators B 111-112, 2005, p. 396-402).*
Sadler (IEEE Transactions on components and packaging technologies, Jun. 2003, vol. 26, No. 2, p. 309-316).*
Chou (Microelectronic Engineering, 61-62, 2002, p. 921-925).*
Golonka, L.J. et al. "LTCC Based Microfluidic System with Optical Detection," Sensors and Actuators B: Chemical, Nov. 2005, vol. 111-112, pp. 396-402.
Martinez-Cisneros, C.S. et al., "LTCC Microflow Analyzers with Monolithic Integration of Thermal Control," Sensors and Actuators A: Physical, Jul. 2007, vol. 138, No. 1, pp. 63-70.
PCT International Search Report and Written Opinion, PCT Application No. PCT/IN2008/000666, Apr. 1, 2009, 10 pages.
Sadler, D.J. et al., "Thermal Management of BioMEMS: Temperature Control for Ceramic-Based PCR and DNA Detection Devices," IEEE Transaction on Components and Packaging Technologies, Jun. 2003, vol. 26, No. 2, pp. 309-316.

* cited by examiner

*Primary Examiner* — Michael Wilson
(74) *Attorney, Agent, or Firm* — Fenwick & West LLP

(57) ABSTRACT

Instant invention is about a micro chip comprising plurality of layers of LTCC wherein a reaction chamber is formed in plurality of top layers to load samples. A heater embedded in at least one of the layers below the reaction chamber and a temperature sensor is embedded in at least one of the layers between the heater and the reaction chamber for analyzing the sample. The temperature sensor can be placed outside the chip to measure the chip temperature.

7 Claims, 9 Drawing Sheets

(a)

(b)

MICRO CHIP

FIELD OF INVENTION

The disclosure is related to a micro PCR (Polymerase chain reaction) chip comprising a plurality of layers made of low temperature co-fired ceramics (LTCC). The disclosure also provides for a portable real-time PCR device with disposable LTCC micro PCR chip.

BACKGROUND OF THE INVENTION

Recent advances in molecular and cell biology have taken place as a result of the development of rapid and efficient analytical techniques. Due to miniaturization and multiplexing techniques like gene chip or biochip enable the characterization of complete genomes in a single experimental setup. PCR is a molecular biology method for the in-vivo amplification of nuclear acid molecules. The PCR technique is rapidly replacing other time consuming and less sensitive techniques for identification of biological species and pathogens in forensic, environmental, clinical and industrial samples. Among the biotechniques, PCR has become the most important analytical step in life sciences laboratories for a large number of molecular and clinical diagnostics. Important developments made in PCR technology like real-time PCR, have led to rapid reaction processes compared to conventional methods. During the past several years, microfabrication technology has been expanded to the miniaturization of the reaction and analysis system such as PCR analysis with the intention of further reducing analysis time and consumption of reagents. Several research groups have been working on the 'lab-on-a-chip' devices and have led to number of advances in the fields of miniaturized separation and reaction systems.

In most PCR's available now, instantaneous temperature changes are not possible because of sample, container, and cycler heat capacities, and extended amplification times of 2 to 6 hours result. During the periods when sample temperature is making a transition from one temperature to another, extraneous, undesirable reactions occur that consume important reagents and create unwanted interfering compounds.

OBJECTS OF INVENTION

An object of the present invention was to provide for a micro chip allowing faster PCR performance.

Another object of the present invention was to provide for an improved micro chip.

One of the main objects of the invention is to develop a micro chip comprising plurality of layers of LTCC.

Still another object of the instant invention is to develop a method of fabricating the micro chip.

Yet another object of the instant invention is to develop a micro PCR device comprising the micro chip.

Still another object of the present invention is to develop a method of diagnosing disease conditions using the micro-PCR device.

STATEMENT OF INVENTION

Accordingly the invention provides for a micro chip comprising a plurality of layers made of low temperature co-fired ceramics (LTCC), wherein a reaction chamber is formed in a plurality of reaction chamber layers for loading a sample, a conductor is embedded in at least one conductor layer placed below the reaction chamber and a heater is embedded in at least one heater layer placed below the conductor layer(s); a method of fabricating a micro chip comprising the steps: (a) arranging plurality of layers made of low temperature co-fired ceramics (LTCC) and having a well to form a reaction chamber, (b) placing at least one layer of LTCC comprising heater below the chamber, (c) placing one or several conductor layer(s) between the heater and the reaction chamber, and (d) interconnecting the layers to form the micro chip; a micro PCR device comprising: (a) a micro chip comprising plurality of layers of LTCC, wherein a reaction chamber is formed in a plurality of layers for loading sample, conductor is embedded in at least one layer placed below the reaction chamber and heater is embedded in at least one layer placed below the conductor layer(s); (b) a temperature sensor embedded in the micro chip or placed outside the chip to measure the chip temperature, (c) a control circuit to control the heater based on the temperature sensor input; and (d) an optical system to detect fluorescence signal from the sample; and a method of detecting an analyte in a sample or diagnosing a disease condition using a micro-PCR device, the method comprising steps of: (a) loading a sample comprising nucleic acid onto a micro chip comprising plurality of LTCC layers, (b) amplifying the nucleic acid by running the micro-PCR device; and (c) determining the presence or absence of the analyte based on a fluorescence reading of the amplified nucleic acid, or determining the presence or absence of a pathogen based on a fluorescence reading of the amplified nucleic acid to diagnose the disease condition.

BRIEF DESCRIPTION OF THE ACCOMPANYING DRAWINGS

The invention will now be described with reference to the accompanying drawings.

DETAILED DESCRIPTION OF THE INVENTION

Figure 1:
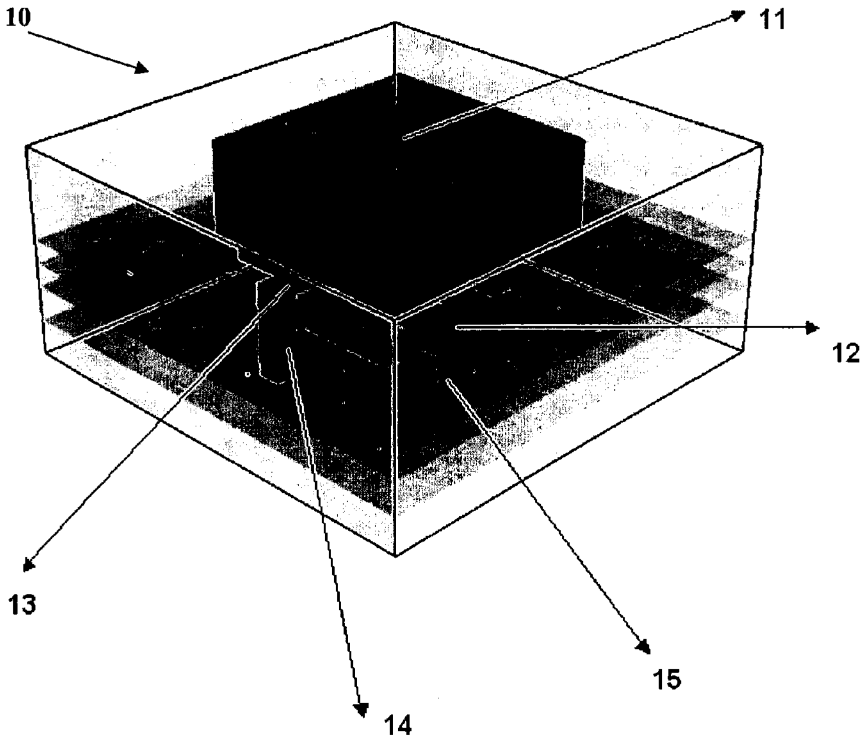
FIG. 1 shows an orthographic view of an embodiment of the LTCC micro PCR chip.

The present invention relates to a micro chip comprising a plurality of layers made of low temperature co-fired ceramics (LTCC), wherein a reaction chamber is formed in a plurality of reaction chamber layers for loading a sample, a conductor is embedded in at least one conductor layer placed below the reaction chamber and a heater is embedded in at least one heater layer placed below the conductor layer(s).

In one embodiment of the present invention, the reaction chamber is covered with a transparent sealing cap.

In one embodiment of the present invention, the chip comprises a temperature sensor.

In one embodiment of the present invention, the temperature sensor is embedded in at least one sensor layer of the chip.

In one embodiment of the present invention, the temperature sensor is a thermistor.

In one embodiment of the present invention, the chip provide for contact pads to connect external control circuit to the temperature sensor and the heater.

In one embodiment of the present invention, the temperature sensor is placed outside the chip to measure the chip temperature.

In one embodiment of the present invention, the reaction chamber is surrounded with conductor rings.

In one embodiment of the present invention, the conductor rings are connected to the conductor layer(s) with posts.

In one embodiment of the present invention, the conductor is made of material selected from group comprising gold, silver, platinum and palladium or alloys thereof.

In one embodiment of the present invention, there is a gap between the reaction chamber base and the heater, and said gap is ranging from about 0.2 mm to about 0.7 mm.

In one embodiment of the present invention, the sample is food or a biological sample selected from a group comprising blood, serum, plasma, tissues, saliva, sputum and urine.

In one embodiment of the present invention, the reaction chamber has a volume ranging from about 1 μl to about 25 μl.

The present invention also relate to a method of fabricating a micro chip comprising the steps:

a) arranging plurality of layers made of low temperature co-fired ceramics (LTCC) and having a well to form a reaction chamber,
b) placing at least one layer of LTCC comprising heater below the chamber,
c) placing one or several conductor layer(s) between the heater and the reaction chamber, and
d) interconnecting the layers to form the micro chip.

In one embodiment of the present invention, wherein placing at least one layer of LTCC comprising a temperature sensor between the heater and the reaction chamber or below the heater.

In one embodiment of the present invention, the chamber is surrounded with conducting rings.

One embodiment of the present invention provides posts to connect the conducting rings to the conductor layer(s).

The present invention also relates to a micro PCR device comprising:

a) a micro chip comprising plurality of layers of LTCC, wherein a reaction chamber is formed in a plurality of layers for loading sample, conductor is embedded in at least one layer placed below the reaction chamber and heater is embedded in at least one layer placed below the conductor layer(s);
b) a temperature sensor embedded in the micro chip or placed outside the chip to measure the chip temperature,
c) a control circuit to control the heater based on the temperature sensor input; and
d) an optical system to detect fluorescence signal from the sample.

In one embodiment of the present invention, the device is a hand held device.

In one embodiment of the present invention, the device is controlled with a portable computing platform.

In one embodiment of the present invention, the device is arranged in an array to carry out multiple PCRs.

In one embodiment of the present invention, the micro chip is releasable from the device.

The present invention also relates to a method of detecting an analyte in a sample or diagnosing a disease condition using a micro-PCR device, the method comprising steps of:

a) loading a sample comprising nucleic acid onto a micro chip comprising plurality of LTCC layers,
b) amplifying the nucleic acid by running the micro-PCR device; and
c) determining the presence or absence of the analyte based on a fluorescence reading of the amplified nucleic acid, or determining the presence or absence of a pathogen based on a fluorescence reading of the amplified nucleic acid to diagnose the disease condition.

In one embodiment of the present invention, the nucleic acid is either DNA or RNA.

In one embodiment of the present invention, the method provides for both qualitative and quantitative analysis of the amplified products.

In one embodiment of the present invention, the sample is food or biological sample.

In one embodiment of the present invention, the biological sample is selected from a group comprising blood, serum, plasma, tissues, saliva, sputum and urine.

In one embodiment of the present invention, the pathogen is selected from a group comprising viruses, bacteria, fungi, yeasts and protozoa.

The term "reaction chamber layer" in the disclosure refers to any layer of the micro chip involved in the formation of the reaction chamber and that comes into contact with a sample.

The term "conductor layer" in the disclosure refers to any layer of the micro chip having a conductor embedded in it.

The term "heater layer" in the disclosure refers to any layer of the micro chip having a heater embedded in it.

The Polymerase Chain Reaction (PCR) is a technique discovered to synthesize multiple copies of a specific fragment of DNA from a template. The original PCR process is based on heat stable DNA polymerase enzyme from Thermus aquaticus (Taq), which can synthesize a complimentary strand to a given DNA strand in a mixture containing four DNA bases and two primer DNA fragments flanking the target sequence. The mixture is heated to separate the strands of double helix DNA containing the target sequence and then cooled to allow the primers to find and bind to their complimentary sequences on the separate strands and the Taq polymerase to extend the primers into new complimentary strands. Repeated heating and cooling cycles multiply the target DNA exponentially, since each new double strand separates to become two templates for further synthesis.

A typical temperature profile for the polymerase chain reaction is as follows:

1. Denaturation at 93° C. for 15 to 30 seconds
2. Annealing of Primer at 55° C. for 15 to 30 seconds
3. Extending primers at 72° C. for 30 to 60 seconds As an example, in the first step, the solution is heated to 90-95° C. so that the double stranded template melts ("denatures") to form two single strands. In the next step, it is cooled to 50-55° C. so that short specially synthesized DNA fragments ("primers") bind to the appropriate complementary section of the template ("annealing"). Finally the solution is heated to 72° C. when a specific enzyme ("DNA polymerase") extends the primers by binding complementary bases from the solution. Thus two identical double strands are synthesized from a single double strand.

The primer extension step has to be increased by roughly 60 sec/kbase to generate products longer than a few hundred bases. The above are typical instrument times; in fact, the denaturing and annealing steps occur almost instantly, but the temperature rates in commercial instruments usually are less than 1° C./sec when metal blocks or water are used for thermal equilibration and samples are contained in plastic microcentrifuge tubes.

By micromachining thermally isolated, low mass PCR chambers; it is possible to mass-produce a much faster, more energy efficient and a more specific PCR instrument. Moreover, rapid transitions from one temperature to another ensure that the sample spends a minimum amount of time at undesirable intermediate temperatures so that the amplified DNA has optimum fidelity and purity.

Low Temperature Co-fired Ceramics (LTCC) is the modern version of thick film technology that is used in electronic component packaging for automotive, defense, aerospace and telecommunication industry. It is an alumina based glassy ceramic material that is chemically inert, bio-compatible, thermally stable (>600° C.), has low thermal conductivity (<3 W/mK), good mechanical strength and provides good hermiticity. It is conventionally used in packaging chip level electronic devices where in they serve both structural and electrical functions. The present inventors have recognized the suitability of LTCC to be used for micro PCR chip applications, and, to the best knowledge of the inventors, LTCC has not been used before for such purpose. The basic substrates in LTCC technology is preferably unfired (green) layers of glassy ceramic material with a polymeric binder. Structural features are formed by cutting/punching/drilling these layers and stacking multiple layers. Layer by layer process enables creating three-dimensional features essential for MEMS (Micro Electro Mechanical Systems). Features down to 50 microns can be readily fabricated on LTCC. Electrical circuits are fabricated by screen-printing conductive and resistive paste on each layer. Multiple layers are interconnected by punching vias and filling them with conducting paste. These layers are stacked, compressed and fired. Processing of stacks of up to 80 layers has been reported in the literature1. The fired material is dense and has good mechanical strength.

Typically the PCR product is analyzed using gel electrophoresis. In this technique, DNA fragments after PCR are separated in an electric field and observed by staining with a fluorescent dye. A more suitable scheme is to use a fluorescent dye that binds specifically to double strand DNA to monitor the reaction continuously (real-time PCR). An example of such a dye is SYBR GREEN that is excited by 490 nm blue light and emits 520 nm green light when bound to DNA. The fluorescence intensity is proportional to the amount of double stranded product DNA formed during PCR and hence increases with cycle number.

FIG. 1 shows an orthographic view of an embodiment of the micro PCR chip indicating reaction chamber (11) or well. The figure indicates the assembly of the heater (12) and a temperature sensor thermistor (13) inside the LTCC Micro PCR chip. The heater conductor lines (15) and the thermistor conductor lines (14) are also indicated. These conductor lines will help in providing connection to the heater and the thermistor embedded in the hip with external circuitry.

Figure 2:
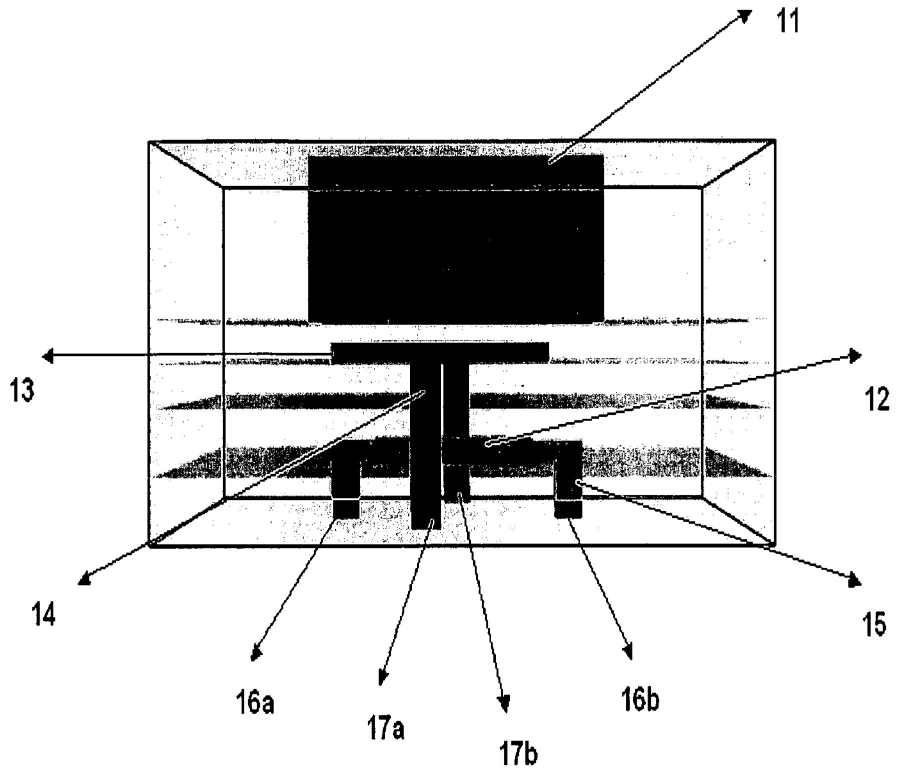
FIG. 2 shows a cross-section of an embodiment of the LTCC micro PCR chip.

Referring to FIG. 2 which shows a cross-sectional view of an embodiment of the LTCC micro PCR chip wherein (16*a* & 16*b*) indicate the contact pads for the heater (12) and (17*a* & 17*b*) indicate the contact pad for the thermistor (13)

Figure 3:
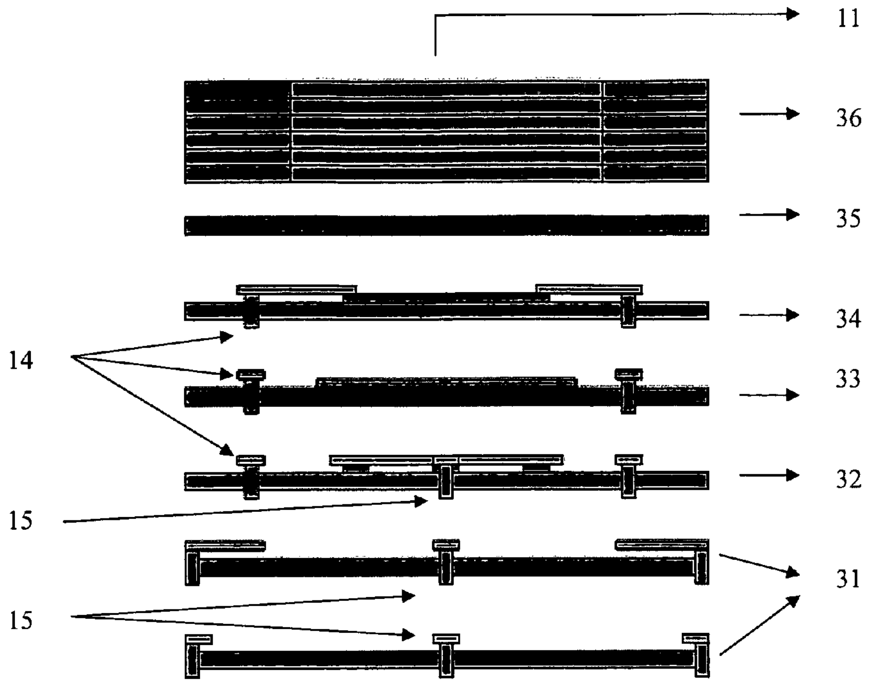
FIG. 3 shows a layer-by-layer design of an embodiment of the LTCC micro PCR chip.

Referring to FIG. 3, which shows the layer-by-layer design of an embodiment of the LTCC micro PCR chip wherein the chip, consists of 12 layers of LTCC tapes. There are two base layers (31), three mid layers having the heater layer (32), a conductor layer (33) and a layer having thermistor (34) whereas (35) forms the interface layer to the reaction chamber (11). The reaction chamber layers (36) consist of six layers as shown. The conductor layer (33) is also provided between the heater and the thermistor layers. The heater conductor line (33) and the thermistor conductor lines (32) are also indicated. In the figure shows the conductor lines (32) is placed in either side of the thermistor layer (34). The heater design can be of any shape like "ladder", "serpentine", "line", "plate". Etc. with size varying from 0.2 mm×3 mm to 2 mm×2 mm. The size and shape of the heater can be selected based on the requirements. The requirements could be like depending on the size of the reaction chamber or the sample been tested or the material been used as a conductor layer.

FIG. 3 shows the layer wise design and an image of an embodiment of the packaged chip fabricated. The LTCC chip has well volume of 1 to 25 μl and a resistance variation (heater and thermistor) of around 50%. The resistance values of the heater (~40Ω) and thermistor (~1050Ω) were consistent with the estimated values. The heater is based on thick film resistive element that is employed in conventional LTCC packages. The thermistor system with alumina is used for fabrication of embedded temperature sensors. The measured TCR of the chip was between 1 and 2Ω/° C. The chip was fabricated on DuPont 951 green system. The thermistor layer can be placed any were in the chip or a temperature sensor can be placed outside the chip instead of thermistor inside the chip.

Figure 4:
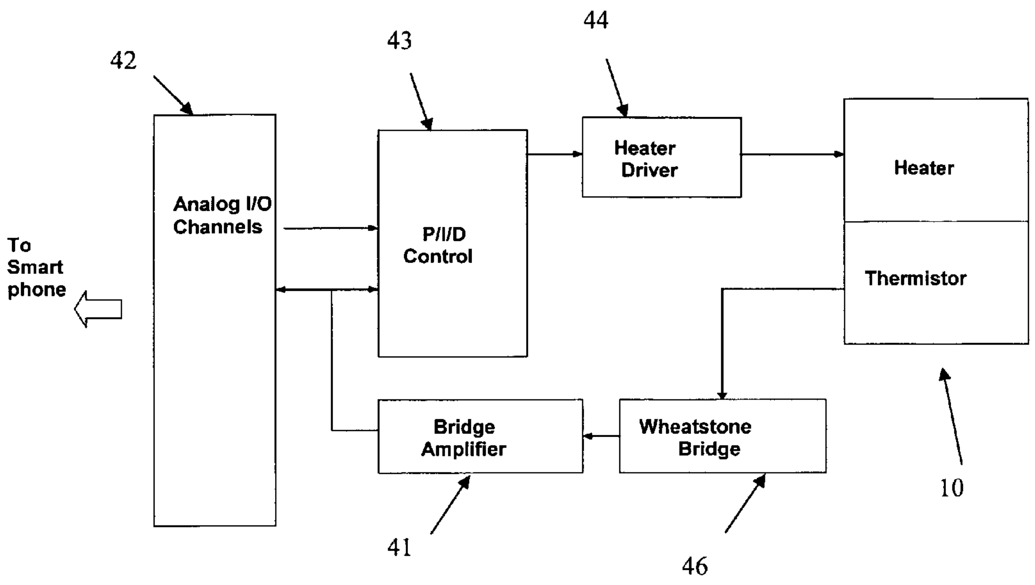
FIG. 4 shows a block diagram of an embodiment of the circuit controlling the heater and thermistor.

Referring to FIG. 4, which shows the block diagram of an embodiment of the circuit controlling the heater and thermistor wherein the thermistor in the LTCC Micro PCR Chip (10) acts as one of the arms in the bridge (46). The amplified output of the bridge from the bridge amplifier (41) is given as input to the PID controller (43), where it is digitized and the PID algorithm provides a controlled digital output. The output is again converted back to analog voltage and this drives the heater using a power transistor present in the heater driver (46). In addition, it is cheaper to process LTCC when compared to silicon processing.

The invention also provides to improve the conventional PCR systems in analysis time, portability, sample volume and the ability to perform throughput analysis and quantification. This is achieved with a portable micro PCR device, with real-time in-situ detection/quantification of the PCR products which comprises the following:

- Disposable PCR chip consisting of reaction chamber/s, embedded heater and a temperature sensor with a transparent sealing cap.
- A handheld electronics unit consisting of the following units
  - Control circuit for the heater and the temperature sensor.
  - Fluorescence optical detection system.
- A smart phone or PDA (personal digital assistant) running a program to control the said handheld unit.

The disposable PCR chip consists of a reaction chamber that is heated by an embedded heater and monitored by an embedded thermistor. It is fabricated on Low Temperature Cofired Ceramic (LTCC) system and packaged suitably with a connector with contacts for heater and temperature sensor.

The embedded heater is made of resistor paste like CF series from DuPont compatible to LTCC. Any green ceramic tape system can be used such as DuPont 95, ESL (41XXX series), Ferro (A6 system) or Haraeus. The said embedded temperature sensor is a thermistor fabricated using a PTC (Positive Temperature Coefficient) resistance thermistor paste (E.g.: 509X D, are ESL 2612 from ESL Electroscience) for Alumina substrates. NTC: Negative Temperature Coefficient of resistance paste like NTC 4993 from EMCA Remex can also be used.

The transparent (300 to 1000 nm wavelength) sealing cap is to prevent evaporation of the sample from the said reaction chamber and is made of polymer material.

The control circuit would consist of an on/off or a PID (Proportional Integral Differential) control circuit, which would control the heater based on the output from a bridge circuit of which the embedded thermistor would form a part. The method of controlling the heater and reading the thermistor value disclosed here is only an example. This should not be considered as the only way to controller or the limitation. Other means and method to control the heater and reading the thermistor value is well applicable to the instant discloser.

The fluorescence optical detection system would comprise of an excitation source of a LED (Light Emitting Diode) and the fluorescence detected by a photodiode. The system would house optical fibers which would be used to project the light on to the sample. Optical fiber can also be used to channel light on to the photodiode. The LED and the photodiode are coupled to optical fiber thought appropriate band pass filter. Accurate measurement of the output signal from the photodetector requires a circuit that has extremely good signal to noise ratio. The fluorescence detection system disclosed here is only an example. This should not be considered as the only way to detect or the limitation. Any fluorescence detector would work unless it is not able to project itself on the sample.

The invention provides a marketable handheld PCR system for specific diagnostic application. PDA has control software running to provide a complete handheld PCR system with real time detection and software control.

Figure 12:
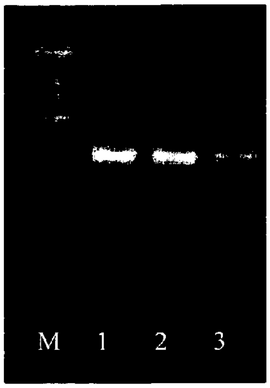
FIG. 12 shows time taken for amplifying Hepatitis B Viral DNA using LTCC chip

By reducing thermal mass and improved heating /cooling rates using the device, the time taken from 2 to 3 hours to finish a 30 to 40-cycle reaction, even for a moderate sample volume of 5-25 μl, was reduced to less than 30 minutes. FIG. 12 shows time taken for amplifying Hepatitis B Viral DNA using LTCC chip of instant invention. The PCR was run for 45 cycles and were able to achieve amplification within 45 minutes. Further, the amplification was observed when the PCR was run for 45 cycles in 20 minutes and 15 minutes also. Conventional PCR duration for HBV (45 cycles) would take about 2 hours.

Miniaturization allows accurate readings with smaller sample sizes and consumption of smaller volumes of costly reagents. The small thermal masses of Microsystems and the small sample sizes allows rapid low-power thermal cycling increasing the speed of many processes such as DNA replication through micro PCR. In addition, chemical processes that depend on surface chemistry are greatly enhanced by the increased surface to volume ratios available on the microscale. The advantages of micro fluidics have prompted calls for the development of integrated microsystem for chemical analysis.

The Micro chip translated into a handheld device, thereby removes the PCR machine from a sophisticated laboratory, thus increasing the reach of this extremely powerful technique, be it for clinical diagnostics, food testing, blood screening at blood banks or a host of other application areas.

Existing PCR instruments with multiple reaction chambers provide multiple DNA experiment sites all running the same thermal protocol and hence are not time efficient. The need arises, to minimize reaction time and intake sample volume.

Instant PCR is designed in future, could have an array of devices with very quick thermal response and highly isolated from the adjacent PCR chips to be able to effectively and independently run multiple reactions with different thermal protocols with minimum cross talk.

The analysis or quantification of the PCR products is realized by practical integration of a real-time fluorescence detection system. This system could also be integrated with quantification and sensing systems to detect diseases like Hepatitis B (FIG. 12), AIDS, tuberculosis, etc. Other markets include food monitoring, DNA analysis, forensic science and environmental monitoring.

Figure 5:
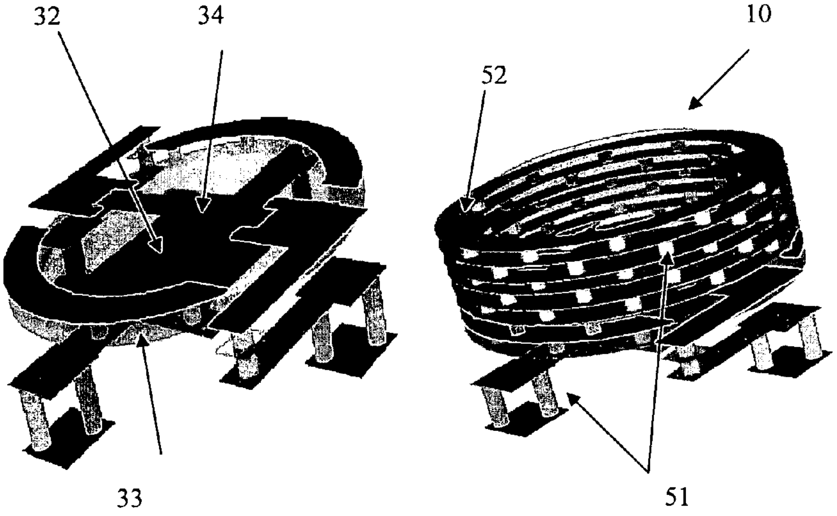
FIG. 5 shows a model of the chip reaction chamber design fabricated.

After determining the uniformity of the temperature profile with in the chip, PCR reactions were carried out on these chips. Lambda DNA fragments and salmonella DNA has been successfully amplified using these chips. FIG. 5 shows the micro chip in 3 dimensional views showing its various connections with the heater, conductor rings, thermistor, and conducting rings (52). It also shows posts (51) that are connecting the conductor rings (52) to the conductor plate (33).

Figure 6:
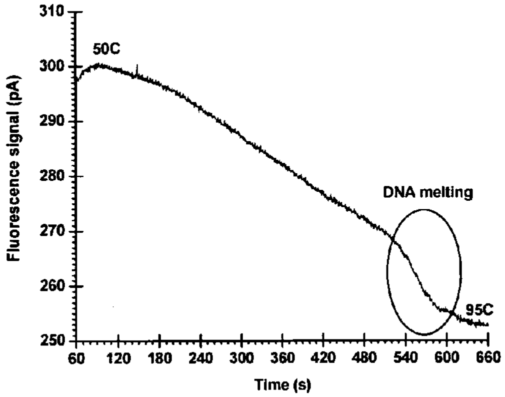
FIG. 6 shows melting of lambda-636 DNA fragment on chip using the integrated heater/thermistor, controlled by the handheld unit.

FIG. 6 shows a comparative plot of the melting of λ-636 DNA fragment on chip using the integrated heater and thermistor.

Figure 7:
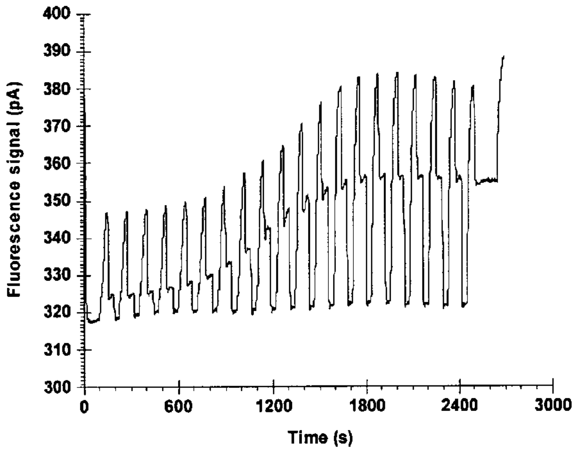
FIG. 7 shows PCR amplification of lambda-311 DNA fragment on chip. (a) Realtime fluorescence signal from the chip; (b) Image of the gel confirming the amplification product.
Figure 7:
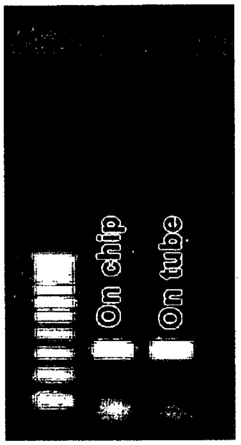

FIG. 7 shows the increase in fluorescence signal associated with amplification of λ-311 DNA. The thermal profile was controlled by the handheld unit and the reaction was performed on a chip (3 μl reaction mixture and 6 μl oil). The fluorescence was monitored using conventional lock-in amplifier.

Figure 11:
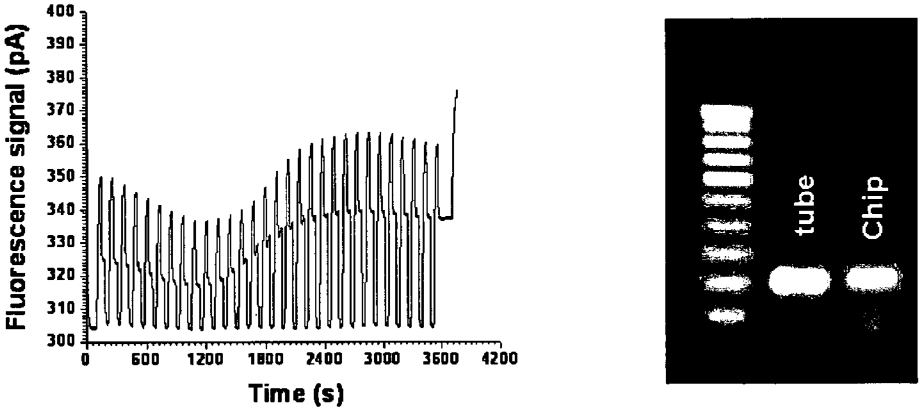
FIG. 11 shows PCR amplification of gene of *Salmonella* using microchip. (a) Realtime fluorescence signal from the chip; (b) Image of the gel confirming the amplification product.

Instant invention also provides for diagnostic system. The procedure adopted for developing the diagnostic system has been to initially standardize thermal protocols for a couple of problems and then functionalize the same on the chip. Primers designed for 16S ribosomal DNA amplified ~300-400 by fragment from *E. coli* and *Salmonella* while the primers for the stn gene amplified ~200 by fragment from *Salmonella typhi*. The products obtained were confirmed by SYBR green fluorescence detection as well as agarose gel electrophoresis. FIGS. 7 and 11 shows the gel picture of the amplified λ-311 DNA and *salmonella* gene using micro-chip.

Thermal profile for amplification of λ-311 DNA:
Denaturation: 94° C. (90 s)
94° C. (30 s)-50° C. (30 s)-72° C. (45 s)
Extension: 72° C. (120 s)

Thermal profile for amplification of *Salmonella* gene:
Denaturation: 94° C. (90 s)
94° C. (30 s)-55° C. (30 s)-72° C. (30 s)
Extension: 72° C. (300 s)

PCR with Processed Blood and Plasma

Figure 8:
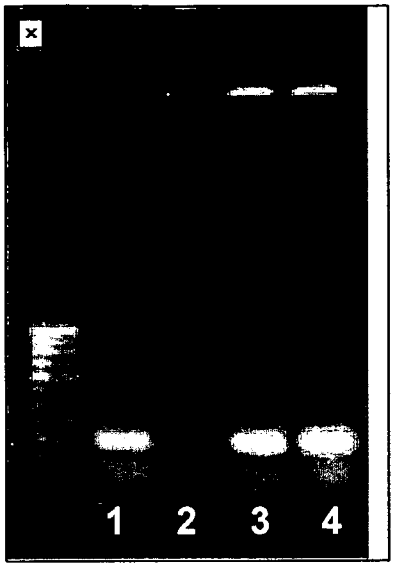
FIG. 8 shows an image of a gel of processed blood and plasma PCR for 16S ribosomal unit of salmonella.
Figure 9:
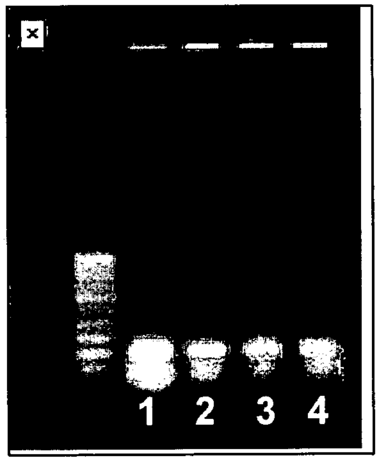
FIG. 9 shows an image of a gel of direct blood PCR for 16S ribosomal unit of salmonella.
Figure 10:
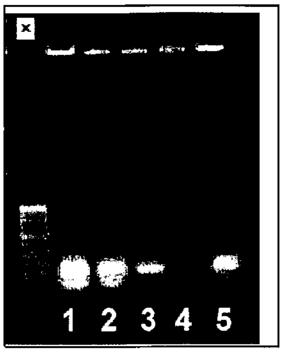
FIG. 10 shows an image of a gel direct plasma PCR for 16S ribosomal unit of *salmonella.*

Blood or plasma were treated with a precipitating agent that can precipitate the major PCR inhibitory substances from these samples. The clear supernatant was used as a template. Using this protocol amplifications were obtained for ~200 by fragment from *Salmonella typhi* (FIG. 8). In FIG. 8, gel electrophoresis image shows 1. control reaction,
2. PCR product-blood without processing,
3. PCR product-processed blood
4. PCR product-processed plasma Blood Direct PCR Buffer A unique buffer has been formulated for direct PCR with blood or plasma samples. Using this unique buffer system direct PCR amplification with blood & plasma has been achieved. With this buffer system, amplification has been obtained up to 50% for blood & 40% for plasma (see FIGS. 9 and 10) using LTCC chip of instant invention. In FIG. 9, gel electrophoresis image shows 1. PCR product—20% blood,
2. PCR product—30% blood,
3. PCR product—40% blood,
4. PCR product—50% blood; and in FIG. 10, gel electrophoresis image shows, 1. PCR product—20% plasma,
2. PCR product—30% plasma,
3. PCR product—40% plasma,
4. PCR product—50% plasma,
5. control reaction The unique buffer comprises a buffer salt, a chloride or sulphate containing bivalent ion, a non-ionic detergent, a stabilizer and a sugar alcohol.

Figure 13:
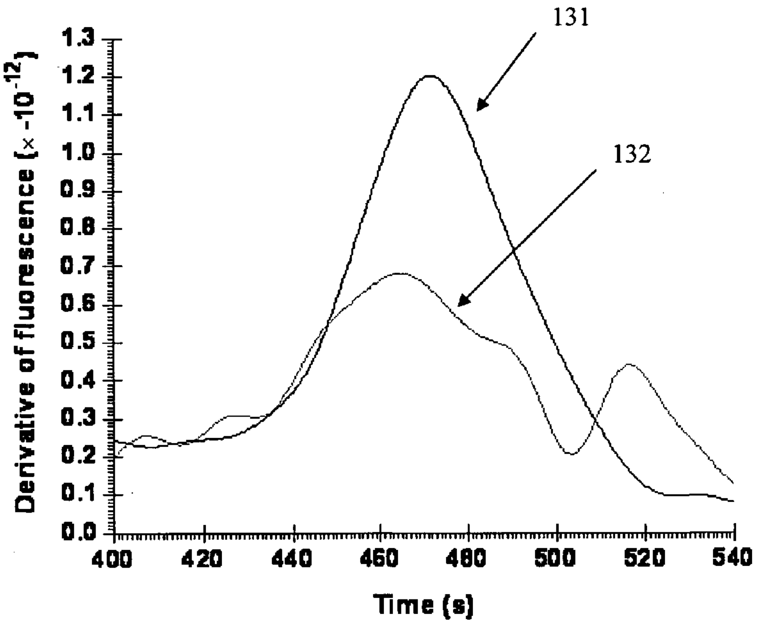
FIG. 13 shows melting curve of LTCC chip for derivative of the fluorescence signal for melting of λ-311 DNA.

FIG. 13 shows melting curve of LTCC chip for derivative of the fluorescence signal for melting of λ-311 DNA. The figure also provides a comparison between the instant invention (131) and the conventional PCR device (132).

Sharper peak: peak value/width (x axis)@half peak value=1.2/43

Shallower peak: peak value/width (x axis)@half peak value=0.7/63

Higher ratio indicates a sharper peak. Also in the graph, the y-axis is the derivative (slope of the melting curve), higher slope indicates sharper melting.

We claim:

1. A chip comprising:

a reaction chamber comprising a plurality of low temperature co-fired ceramic (LTCC) layers;

a plurality of thermal conductor rings surrounding and physically separate from the reaction chamber, the thermal conductor rings connected to each other by a plurality of posts; and a heater indirectly connected to the thermal conductor rings.

2. The chip as claimed in claim 1, wherein the heater is embedded in a heater layer placed below a conductor layer, and the conductor layer is connected to the thermal conductor rings by a plurality of the posts.

3. The chip as claimed in claim 1, wherein the chip comprises a temperature sensor.

4. The chip as claimed in claim 3, wherein the chip comprises:

a plurality of contact pads coupling an external control circuit to the temperature sensor and the heater.

5. The chip as claimed in claim 1, wherein the reaction chamber and the heater are within 0.2 mm to 0.7 mm of each other.

6. The chip as claimed in claim 1, wherein the reaction chamber has a volume ranging from between 1 μl to 25 μl.

7. A method of fabricating the chip as claimed in claim 1.

* * * * *